US010786572B2

United States Patent
Nam et al.

(10) Patent No.: US 10,786,572 B2
(45) Date of Patent: Sep. 29, 2020

(54) ONCOGENIC RAS-INDUCED MALIGNANT CANCERIZATION INHIBITION USING LOW-DOSE RADIATION

(71) Applicant: KOREA HYDRO & NUCLEAR POWER CO., LTD., Gyeongsangbuk-do (KR)

(72) Inventors: Seonyoung Nam, Seoul (KR); Kwang Hee Yang, Seoul (KR); Su-Jae Lee, Seoul (KR); Rae-Kwon Kim, Gyeonggi-do (KR)

(73) Assignee: KOREA HYDRO & NUCLEAR POWER CO., LTD., Gyeongsangbuk-Do (KR)

( * ) Notice: Subject to any disclaimer, the term of this patent is extended or adjusted under 35 U.S.C. 154(b) by 0 days.

(21) Appl. No.: 16/096,532

(22) PCT Filed: Aug. 23, 2016

(86) PCT No.: PCT/KR2016/009301
§ 371 (c)(1),
(2) Date: Oct. 25, 2018

(87) PCT Pub. No.: WO2017/188517
PCT Pub. Date: Nov. 2, 2017

(65) Prior Publication Data
US 2019/0111131 A1    Apr. 18, 2019

(30) Foreign Application Priority Data
Apr. 29, 2016   (KR) .................. 10-2016-0053593

(51) Int. Cl.
*A61K 41/17* (2020.01)
*C12N 15/01* (2006.01)
(Continued)

(52) U.S. Cl.
CPC .......... *A61K 41/17* (2020.01); *A61K 41/0023* (2013.01); *A61N 5/1038* (2013.01);
(Continued)

(58) Field of Classification Search
CPC ............ A61K 41/0019; A61K 41/0023; C12N 15/01; A61N 5/1038; A61N 5/1077; A61N 2005/0661; A61P 35/00
See application file for complete search history.

(56) References Cited

U.S. PATENT DOCUMENTS

| | | | | |
|---|---|---|---|---|
| 7,301,017 | B2* | 11/2007 | Kolesnick | A01K 67/0276 536/24.5 |
| 2010/0240665 | A1* | 9/2010 | Eckhardt | C12N 15/113 514/249 |
| 2015/0159219 | A1* | 6/2015 | Kim | C12Q 1/6883 506/9 |

FOREIGN PATENT DOCUMENTS

| KR | 1020020030511 A | 4/2002 |
|---|---|---|
| KR | 1020130086688 A | 8/2013 |
| KR | 1020150042590 A | 4/2015 |

OTHER PUBLICATIONS

Yin, E. et al., Gene Expression Changes in Mouse Brain After Exposure to Low-Dose Ionizing Radiation, Int. J. Radiat. Biol., Oct. 2003, pp. 759-775, vol. 79, No. 10.
(Continued)

*Primary Examiner* — David P Porta
*Assistant Examiner* — Fani Boosalis
(74) *Attorney, Agent, or Firm* — Standley Law Group LLP; Stephen L. Grant (57) ABSTRACT

The present invention relates to an apparatus for inhibiting oncogene-induced malignant carcinogenesis, including an irradiation unit for applying low-dose radiation to a subject, and to a method of inhibiting oncogene-induced malignant carcinogenesis, including applying low-dose radiation to a
(Continued)

Photographs of plates were taken at the 21th day after seeding and images in a square were acquired using phase contrast microscopy at x200 magnification subject, whereby oncogene-induced malignant carcinogenesis can be inhibited by means of the apparatus and method of the present invention.

10 Claims, 11 Drawing Sheets

(51) Int. Cl.
    *A61N 5/10*     (2006.01)
    *A61P 35/00*     (2006.01)
    *A61K 41/00*     (2020.01)
    *A61N 5/06*     (2006.01)

(52) U.S. Cl.
    CPC ............ *A61N 5/1077* (2013.01); *A61P 35/00* (2018.01); *C12N 15/01* (2013.01); *A61N 5/1031* (2013.01); *A61N 2005/0661* (2013.01)

(56) References Cited

OTHER PUBLICATIONS

Chen, Y. et al., Mitochondrial Redox Signaling and Tumor Progression, Cancers, 2016, pp. 1-15 vol. 8, No. 40.
Suh, Y. et al., KRAS-driven ROS Promote Malignant Transformation, Molecular & Cellular Oncology, Jan. 22, 2015, vol. 2, Issue 2.
Kim, R. et al., Beneficial Effects of Low Dose Radiation in Response to the Oncogenic KRAS Induced Cellular Transformation, Scientific Reports, Oct. 30, 2015, pp. 1-10.
Kim, R. et al., Low Dose Radiation Promotes the Reduction of Malignant Phenotypes of the Transformed Breast Epithelial Cells, Korean Society of Radiation Bioscience, May 21, 2015.

\* cited by examiner

Colony number (blue square) and size (red square) were computationally measured with the whole image of three independent plates using the Image J program. Over 80 μm² colonies were counted and used for the average colony size measurement.

ONCOGENIC RAS-INDUCED MALIGNANT CANCERIZATION INHIBITION USING LOW-DOSE RADIATION

TECHNICAL FIELD

The present invention relates to an apparatus for inhibiting oncogene-induced malignant carcinogenesis, comprising an irradiation unit for applying low-dose radiation to a subject, and to a method of inhibiting oncogene-induced malignant carcinogenesis, comprising applying low-dose radiation to a subject.

BACKGROUND ART

1. Low-Dose Radiation

Although definitive effects and carcinogenesis due to high-dose radiation exposure are well known, the direct effect of low-dose radiation of 100 mSv or less on the human body has not yet been scientifically proven. Furthermore, the dose of medical radiation exposure due to the development of medical devices has remarkably increased, and therefore, more research into the effects of low-dose radiation exposure is needed.

2. Need to Develop Therapy Targeting K-Ras

Cancer cells are constantly dividing and proliferating, and in accordance with reports in various papers, models of cancer proliferation and metastasis to other organs are presented in experimental animal models. In particular, cancer cells induced by the oncogene K-Ras are surprisingly resistant to cancer treatment methods, including anticancer drug treatment and radiotherapy. Recently, it has been recognized that cancer may recur even if cancer cells are killed using a variety of conventional treatment methods such as surgery, radiotherapy, chemotherapy and the like. Thus, cancer cells induced by K-Ras are prone to malignancy and metastasis, and are thus considered to be the cause of recurrence, and thus there is growing interest in developing therapeutic protocols for treating cancer targeting K-Ras.

3. K-Ras-Mediated Tumor Microenvironment and Metastasis and Maintenance of Cancer Cells K-Ras in normal tissues regulates cell growth and differentiation, but cancer cells are affected by tumor microenvironment factors around the tumor cells to thus activate abnormal division and maintenance pathways, rapidly accumulating, becoming malignant, developing resistance to anticancer therapy, and ultimately leading to cancer recurrence. However, specific mechanisms for entities and interactions of tumor microenvironment factors controlling the metastasis and maintenance of cancer cells have not yet been studied.

A number of papers and patent documents are referenced and cited throughout this specification. The disclosures of the cited papers and patent documents are incorporated herein by reference in their entirety to further clarify the level and scope of the subject matter to which the present invention pertains.

DISCLOSURE

Technical Problem

The present inventors have, through extensive research, developed a method of inhibiting malignant carcinogenesis induced by K-Ras, and thus have ascertained that malignant carcinogenesis induced by K-Ras may be inhibited through low-dose irradiation, thereby culminating in the present invention.

Accordingly, an objective of the present invention is to provide an apparatus for inhibiting oncogene-induced malignant carcinogenesis, comprising an irradiation unit for applying low-dose radiation to a subject.

Another objective of the present invention is to provide a method of inhibiting oncogene-induced malignant carcinogenesis, comprising applying low-dose radiation to a subject.

The other objectives and advantages of the present invention will become more apparent from the following detailed description of the invention, claims and drawings.

Technical Solution

An aspect of the present invention provides an apparatus for inhibiting oncogene-induced malignant carcinogenesis, comprising an irradiation unit for applying low-dose radiation to a subject.

Culminating in the present invention, thorough research into the development of a method of inhibiting malignant carcinogenesis induced by K-Ras, carried out by the present inventors, resulted in the finding that K-Ras-induced malignant carcinogenesis may be inhibited through low-dose irradiation. The present invention is characterized by using low-dose radiation. As used herein, the term "low-dose radiation" refers to radiation of a relatively low cumulative dose compared to the cumulative dose of radiation that is conventionally used in the diagnosis and treatment of a patient, and "low-dose radiation" is typically used as a general term without particularly representing a cumulative dose. In the apparatus for inhibiting malignant carcinogenesis according to the present invention, the shape, structure and size of the "irradiation unit" are not particularly limited, so long as it is any means for applying radiation of 100 mGy or less to a subject. The irradiation apparatus used to inhibit oncogene-induced malignant carcinogenesis, including the irradiation unit for applying radiation of 100 mGy or less, is to be understood to be incorporated in the scope of the present invention.

In an embodiment of the present invention, the low-dose radiation has a cumulative dose of 100 mGy or less but exceeding 0 mGy. Particularly, the low-dose radiation of the present invention has a cumulative dose of 10 mGy to 100 mGy, and more particularly 30 mGy to 100 mGy.

In an embodiment of the present invention, the oncogene of the present invention is K-Ras. A gene that is likely to convert a normal gene into an oncogene due to various factors is called a proto-oncogene, Ras also being one of these genes. The Ras protein formed by the Ras gene has a molecular weight of 21 kDa, and is specifically expressed only in eukaryotic cells, and three types of Ras proteins (H-Ras, K-Ras, NRas) are present in all animal cells. Ras protein is activated in response to external stimuli activating a tyrosine kinase receptor. When the tyrosine kinase receptor is autophosphorylated by external stimuli, receptor activation is carried out in a manner in which an adaptor protein Grb2 for binding signal proteins forms a complex with SOS protein. The SOS protein is linked with the activated receptor, thus causing GDP/GTP conversion of inactive Ras GDP that binds to the surrounding plasma membrane, thereby activating Ras. The activated Ras plays a role in regulating cell proliferation and differentiation by activating various signal transduction pathways such as the Raf-MAP kinase pathway. Cancer cells induced by K-Ras are known to be surprisingly resistant to cancer treatment methods including anticancer drug treatment and radiotherapy. However, the present inventors first demonstrated the fact that malignant carcinogenesis induced by K-Ras may be prevented through low-dose irradiation.

In an embodiment of the present invention, the radiation of the present invention is selected from the group consisting of alpha rays, beta rays, gamma rays, electron rays, UV rays, and X-rays. More particularly, the radiation of the present invention is gamma rays.

Another aspect of the present invention provides a method of inhibiting oncogene-induced malignant carcinogenesis, comprising applying low-dose radiation to a subject.

As used herein, the term "subject" refers to all organisms in which the process of carcinogenesis of cells due to an oncogene is capable of occurring in the body, and particularly indicates, for example, a mammal containing the Ras gene, by which cell carcinogenesis may progress. As for low-dose radiation used in the present invention, no negative effects on subjects have been reported, and upon real-world application, only a very small amount of radiation is used compared to the dose of radiation conventionally used for the diagnosis and treatment of disease, making it possible to safely apply the low-dose radiation to a subject even before carcinogenesis. Before carcinogenesis due to the oncogene, oncogene-induced malignant carcinogenesis may be inhibited by applying low-dose radiation to a subject.

In an embodiment of the present invention, the subject of the present invention is a mammal other than a human. The oncogene, particularly the Ras gene, is found in a mammal other than a human, and low-dose radiation is applied to a mammal other than a human, thereby obtaining the same effect of inhibiting oncogene-induced malignant carcinogenesis as in humans.

In an embodiment of the present invention, the low-dose radiation of the present invention has a cumulative dose of 100 mGy or less but exceeding 0 mGy. Particularly, the low-dose radiation of the present invention has a cumulative dose of 10 mGy to 100 mGy, and more particularly 30 mGy to 100 mGy. The present inventors have ascertained that the effect of inhibiting oncogene-induced malignant carcinogenesis may be obtained through irradiation of 100 mGy or less, and the effect of inhibiting malignant carcinogenesis is further increased with an increase in the dose of radiation within the above dose range. However, high-dose radiation of about 100 cGy cannot acquire desired effects, whereas low-dose radiation can be concluded to be more effective at inhibiting malignant carcinogenesis.

In an embodiment of the present invention, the oncogene of the present invention is K-Ras.

In an embodiment of the present invention, the radiation of the present invention is selected from the group consisting of alpha rays, beta rays, gamma rays, electron rays, UV rays, and X-rays. More particularly, the radiation of the present invention is gamma rays.

The method of inhibiting oncogene-induced malignant carcinogenesis according to the present invention may be performed using the apparatus for inhibiting oncogene-induced malignant carcinogenesis according to the aspect of the present invention, and a redundant description thereof is omitted in order to avoid excessive complexity of description in this specification.

Advantageous Effects

The features and advantages of the present invention are summarized as follows:
(a) The present invention provides an apparatus for inhibiting oncogene-induced malignant carcinogenesis, comprising an irradiation unit for applying low-dose radiation to a subject;
(b) The present invention provides a method of inhibiting oncogene-induced malignant carcinogenesis, comprising applying low-dose radiation to a subject;
(c) When the apparatus for inhibiting malignant carcinogenesis according to the present invention is used, malignant carcinogenesis induced by an oncogene, particularly K-Ras, can be inhibited;
(d) When the method of inhibiting malignant carcinogenesis according to the present invention is used, malignant carcinogenesis induced by an oncogene, particularly K-Ras, can be inhibited;
(e) When the apparatus and method of the present invention are used, K-Ras-induced malignant carcinogenesis can be inhibited, thus suppressing cancer migration and invasion and preventing cancer metastasis and recurrence.

BEST MODE

A better understanding of the present invention will be given through the following examples, which are set forth merely to illustrate the present invention but are not to be construed as limiting the scope of the present invention based on the gist of the present invention, as will be apparent to those skilled in the art.

Example 1

Acquisition of Tumorigenicity

Figure 1A:
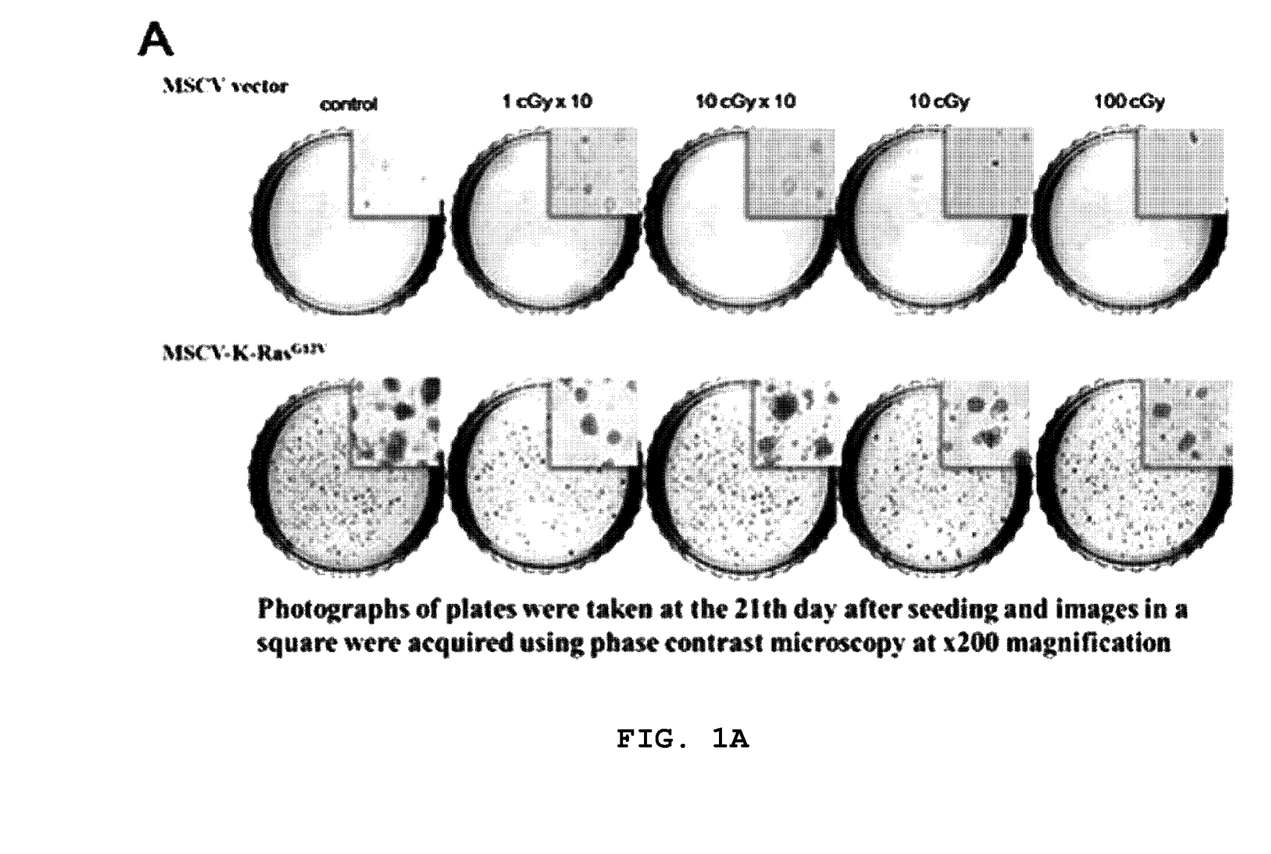
FIGS. 1A and 1B show the extent of tumorigenicity resulting from viral infection with a K-Ras G12V oncogene after applying low-dose radiation at a cumulative dose of 100 mGy and relatively high-dose radiation at 1 Gy (=1000 mGy) to the normal breast cell line MCF10A.

Low-dose radiation at a cumulative dose of 100 mGy (=10 cGy) and relatively high-dose radiation at 1 Gy (=1000 mGy) were applied to the normal breast cell line MCF10A and then the cells were subjected to viral infection with KRas G12V as the oncogene so as to acquire tumorigenicity. In order to evaluate whether low-dose radiation was able to inhibit tumorigenicity, an anchorage-independent growth assay was performed, from which tumorigenesis itself was confirmed to be inhibited by low-dose radiation (FIG. 1A).

Figure 1B:
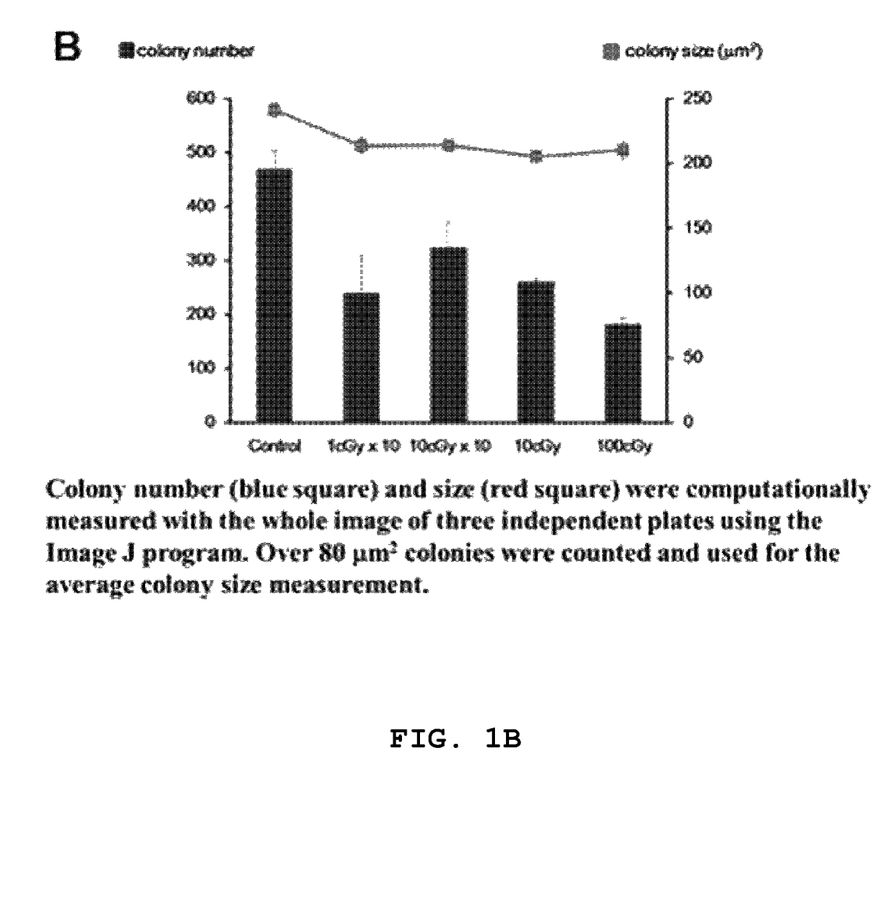

The number and sizes of colonies were computationally measured with the images of three independent plates. As a result thereof, the number and sizes of colonies were significantly increased in cells in which the oncogene K-Ras G12V was over-expressed, whereas the number and size thereof were decreased in low-dose-irradiated cells (FIG. 1B).

Example 2

Migration and Invasion Assay

Figure 2A:
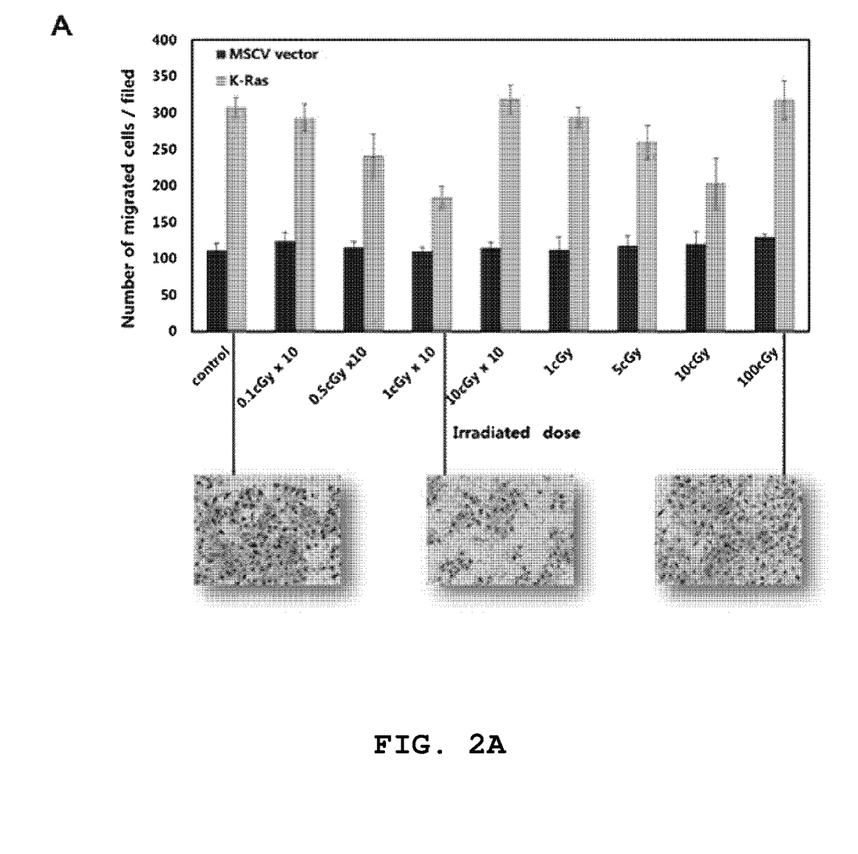
FIGS. 2A and 2B show the results of migration and invasion assay in order to evaluate whether the low-dose radiation applied to normal cells is able not only to inhibit tumorigenicity but also to affect metastatic migration and invasion of transformed cells.
Figure 2B:
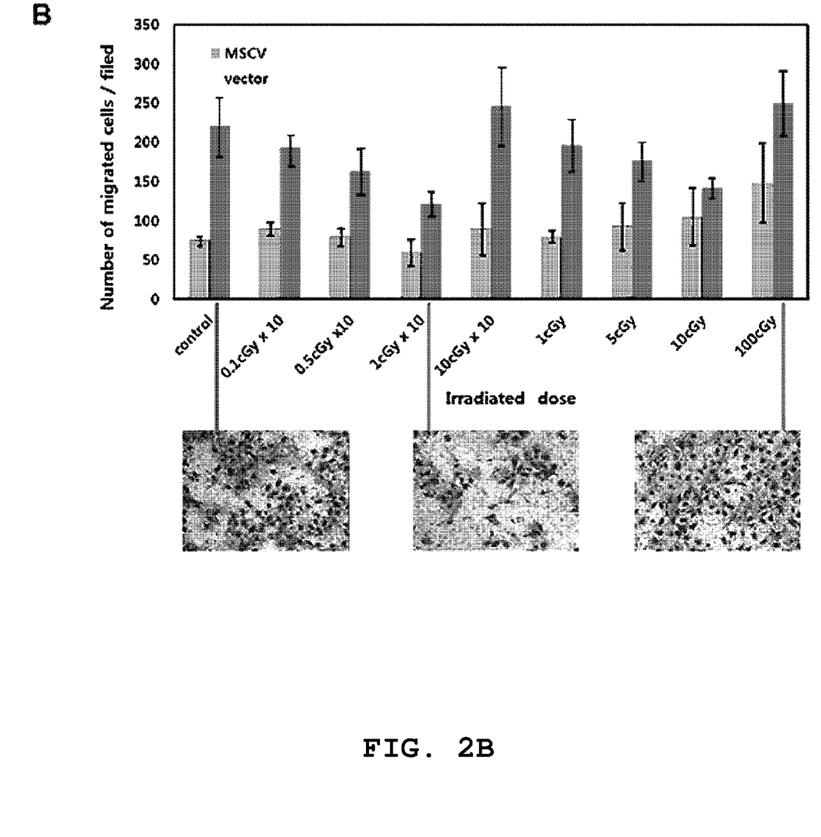

In order to verify the effect of low-dose radiation on inhibiting malignant transformation, radiation was applied at various doses. In respective groups, 1 mGy, 5 mGy, 10 mGy, and 100 mGy were applied 10 times each, and thus final doses were 10 mGy, 50 mGy, 100 mGy, and 1000 mGy (=1 Gy). Individual differences were evaluated through single irradiation in the same dose as in fractionated irradiation. Furthermore, in order to evaluate the response of the low-dose-irradiated cells on the oncogene K-Ras G12V, carcinogenesis was progressed. Thereafter, migration and invasion were assayed using a Boyden Chamber available from Corning. A migration assay method, for measuring the extent of movement of the membrane in the chamber, and an invasion assay method, for measuring the number of cells that migrated through a Matrigel coating in the chamber, were used. In the chamber, $1 \times 10^4$ cells were used. The low-dose radiation at a cumulative dose of 100 mGy or less was confirmed to inhibit metastatic migration, and the effect thereof was increased when approaching 100 mGy (FIG. 2A). Also, the cell line exposed to relatively high-dose radiation of 1 Gy showed metastatic migration similar to that of the untreated control group (FIG. 2B). Specifically, low-dose radiation was confirmed to inhibit metastatic potential upon carcinogenesis of the normal cells, unlike high-dose radiation (FIGS. 2A and 2B).

Example 3

Wound-Healing Assay

Figure 3A:
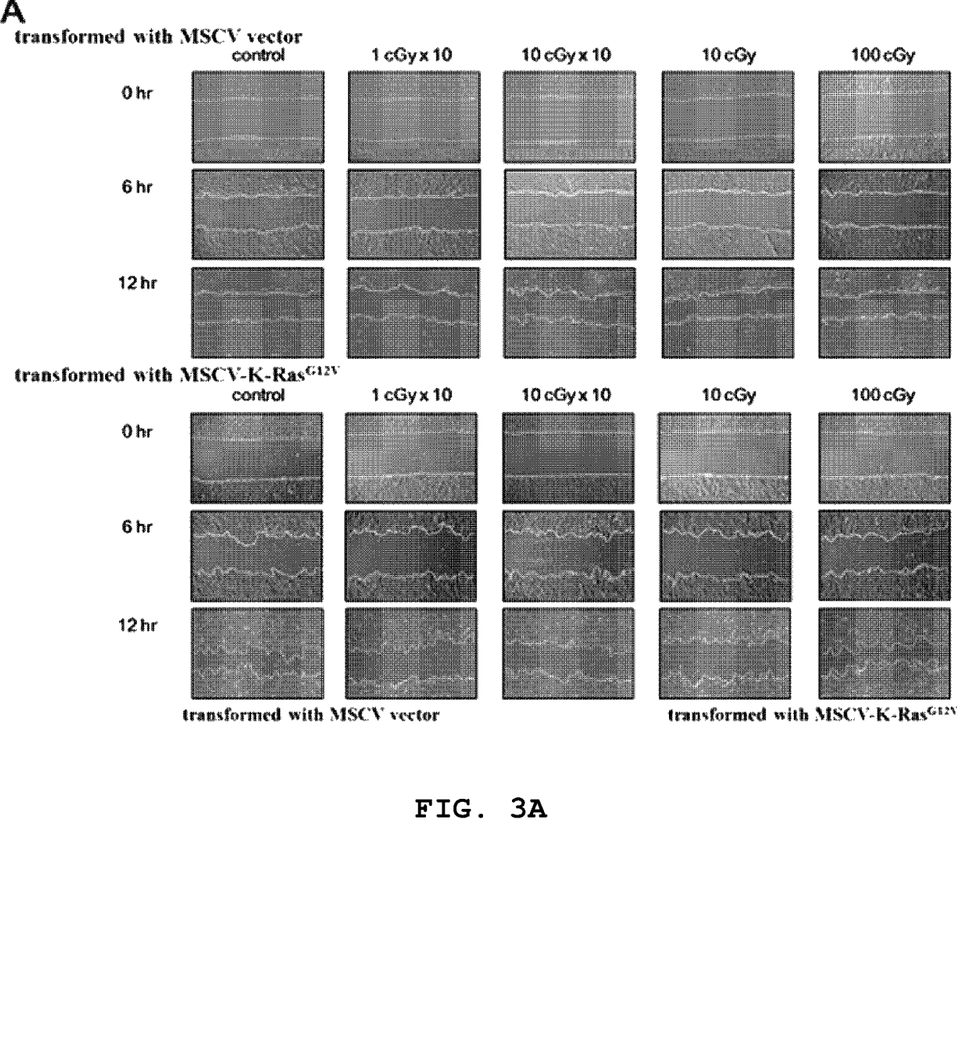
FIGS. 3A and 3B show the results of a wound-healing assay, performed to evaluate changes in cell migration using low-dose radiation because migration of transformed cells is known to increase, showing that changes in the cell migration are delayed.
Figure 3B:
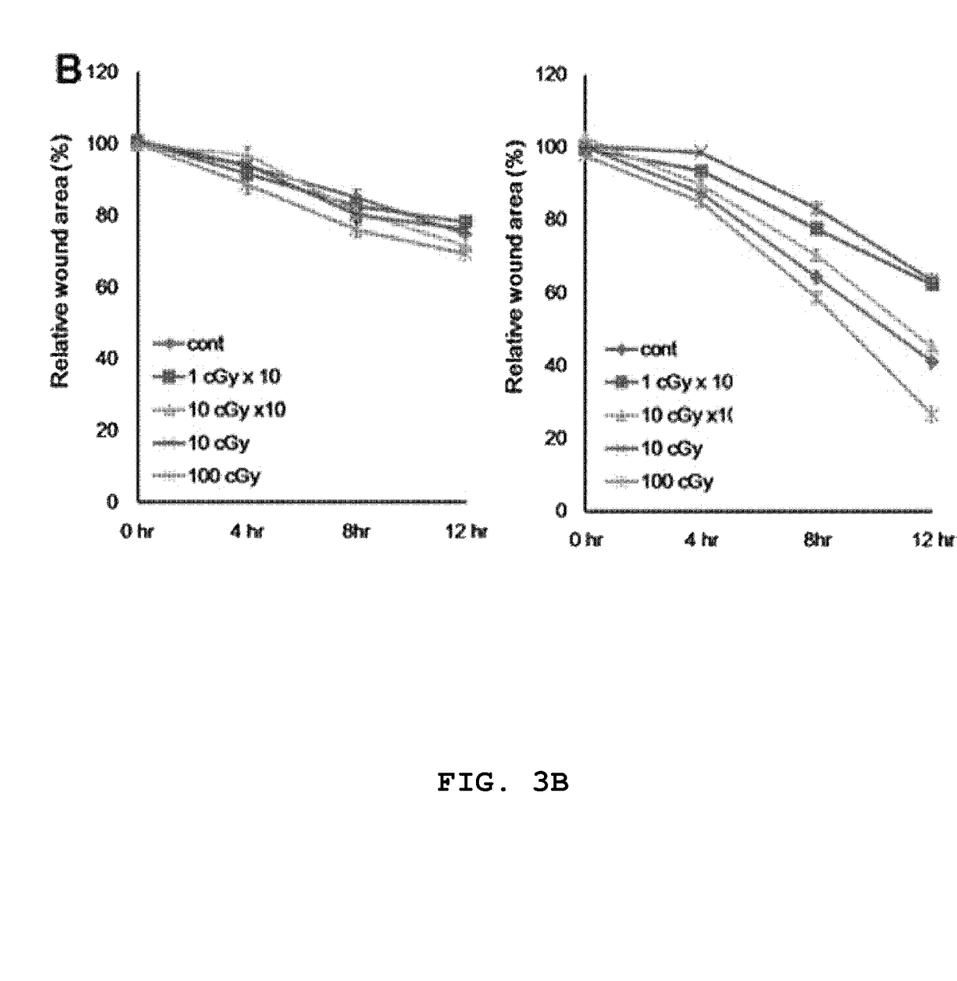

In order to evaluate changes in cell migration using low-dose radiation because migration of transformed cells is known to increase, a wound-healing assay was performed. The program used for the assay was Motic Images Plus 2.0. (A) In the test group transformed with the oncogene K-Ras, motility was decreased through low-dose irradiation, unlike the control group (FIG. 3A). (B) Based on the results of measurement of cell migration over time in the remaining portion of the wound, in the transformed cells treated with low-dose radiation, regardless of whether fractionated irradiation or single irradiation was performed, motility was significantly inhibited compared to the control group not subjected to irradiation (FIG. 3B).

Example 4

Analysis of Pretreatment Effect of Low-Dose Radiation

Figure 4A:
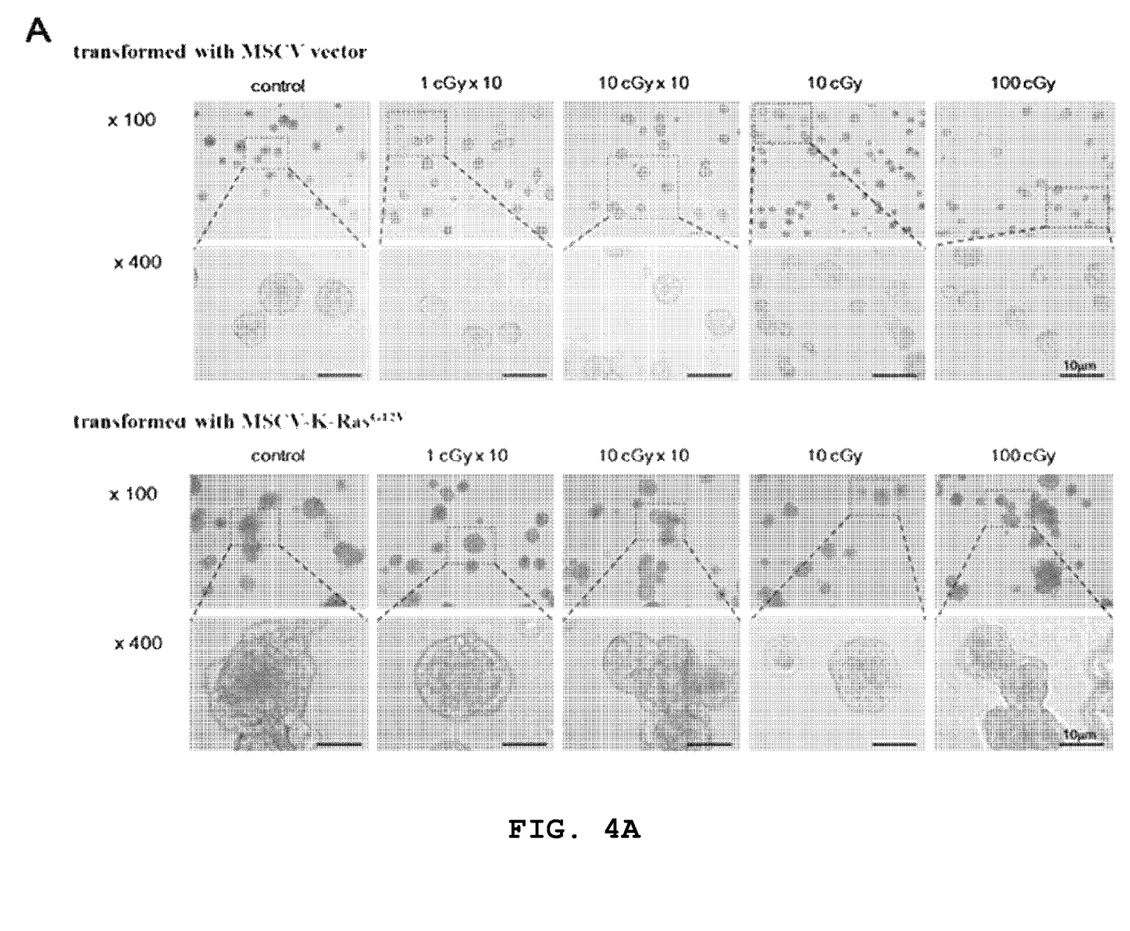
FIGS. 4A to 4C show results in which, when normal breast cells acquire tumorigenicity and metastatic potential due to the oncogene, malignancy of transformed cells may be suppressed by pretreatment with low-dose radiation.
Figure 4B:
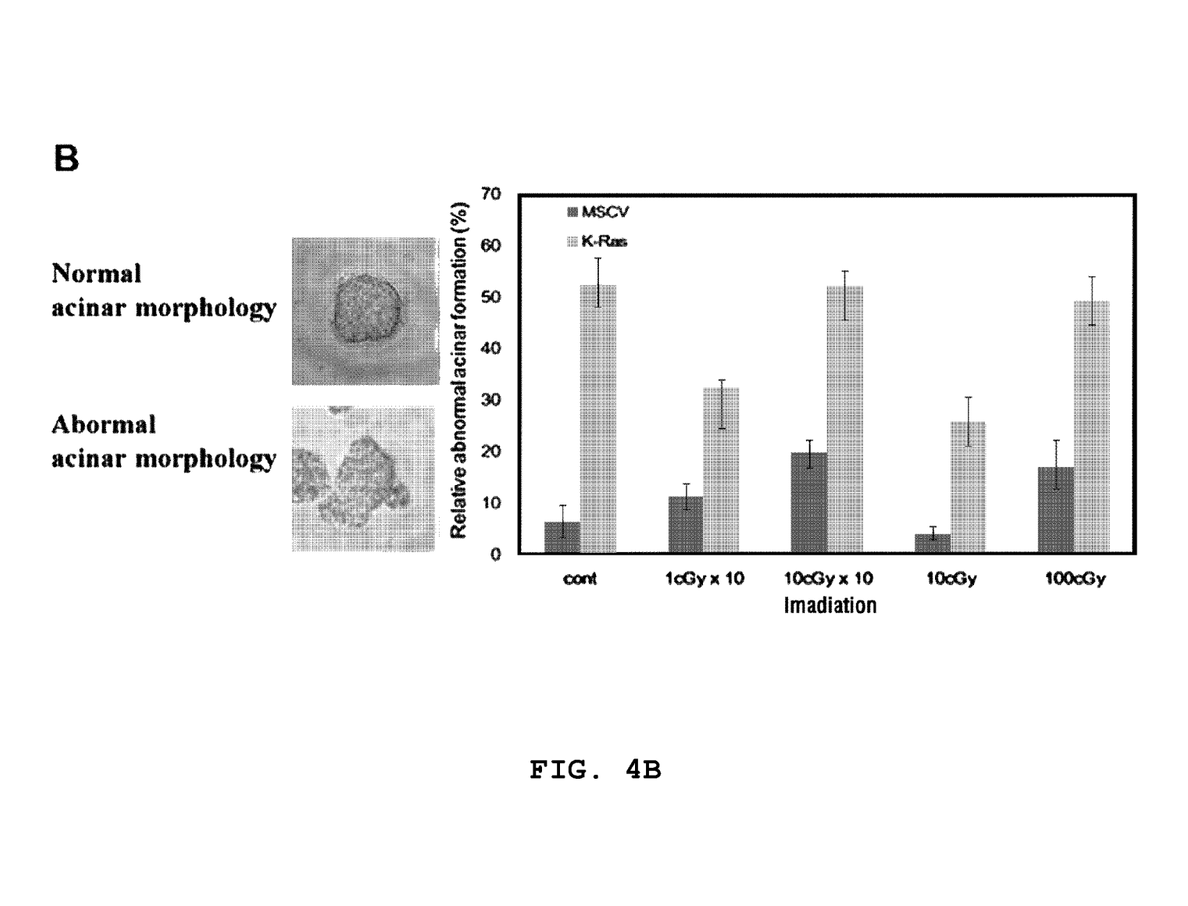
Figure 4C:
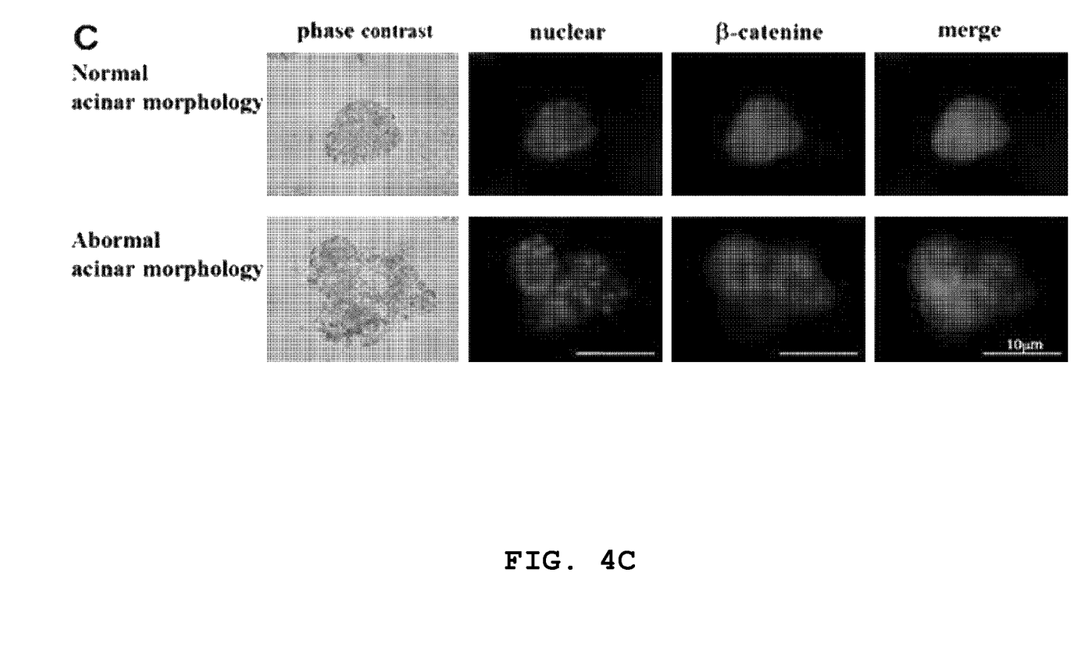

Whether low-dose radiation was able to inhibit the oncogene-transformed cells was evaluated. (A) The transformed cells were incubated using an extracellular matrix and thus abnormal acinar morphologies were observed. (B) Based on the results of measurement of abnormal acinar forms larger than the average size of normal acinar forms determined using 10 microscope images (Olympus ix71), low-dose radiation was confirmed to inhibit malignant carcinogenesis by reducing malignantly transformed cells, that is, acinar forms (FIG. 4B). (C) A phase-contrast microscope capable of adjusting the Z-axis as well as the X-axis and Y-axis control of an object was used to observe abnormal acinar forms of the cells through fluorescence staining of protein beta-catenin associated with cell-to-cell contact based on the external appearance of the cells. As a result thereof, the abnormal acinar morphology which became malignant was observed by showing the expression of beta-catenin in the contact site in the abnormal acinar region, indicating that abnormal acinar morphology is formed upon malignant carcinogenesis (FIG. 4C).

Example 5

Figure 5:
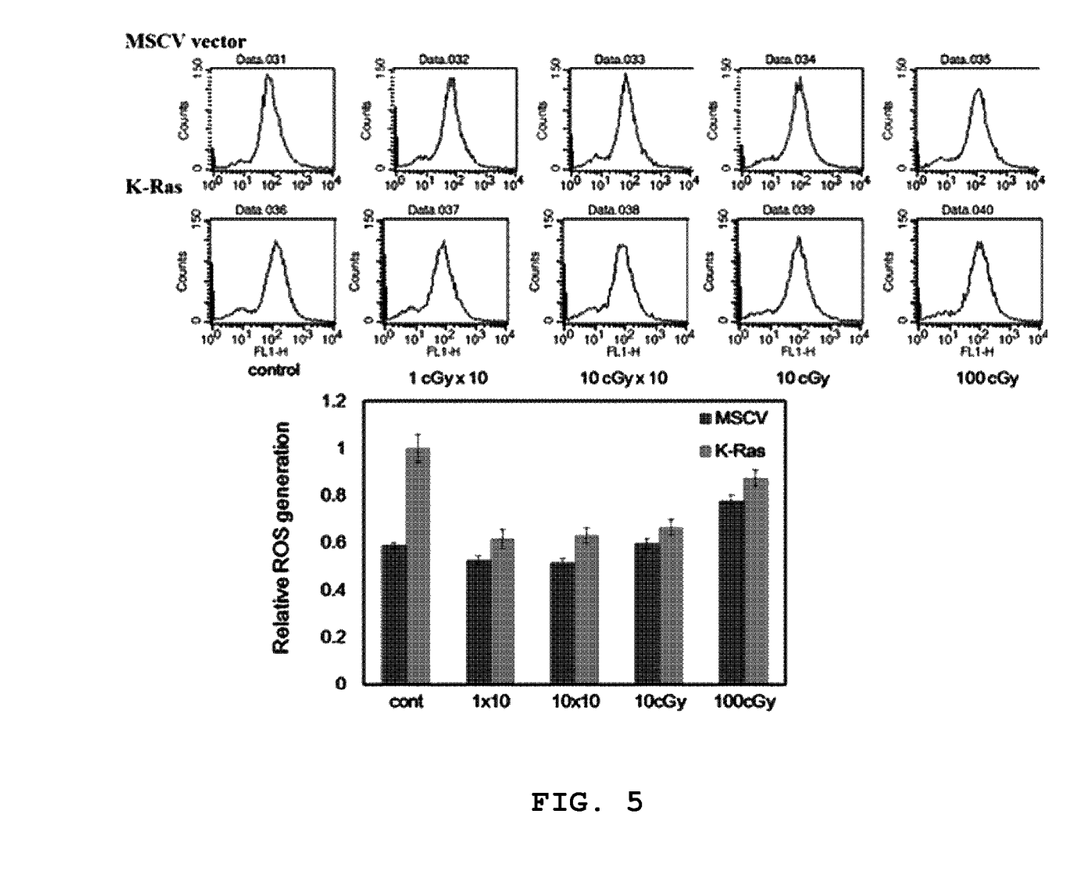
FIG. 5 shows the effects of low-dose radiation on the generation and maintenance of reactive oxygen species (ROS) in transformed cells.

Analysis of ROS Generation and Maintenance of Transformed Cells Through Low-Dose Irradiation The effect of low-dose radiation on the generation and maintenance of reactive oxygen species in the transformed cells was tested. (A) The low-dose-irradiated cells were reacted with a DCF-DA material capable of measuring reactive oxygen species and then measured using a flow cytometer capable of measuring fluorescence. A flow cytometer was used to measure a predetermined amount of cells. The cells for the measurement, which were bound, were tested using a reagent for an antigen-antibody reaction to determine the specificity of cells. Based on the measurement results, low-dose radiation was confirmed to reduce the level of reactive oxygen species in the transformed cells (FIG. 5). Unusually, even when using relatively high-dose radiation at a cumulative dose of 1000 mGy (=1 Gy), the generation of reactive oxygen species was somewhat reduced compared to the control group (FIG. 5). This can be perceived as a result of intricate interactions because changes in the level of reactive oxygen species occur not only due to the oncogene but also due to the radiation.

Example 6

Analysis of Key Protein of Signal Transduction System

Figure 6:
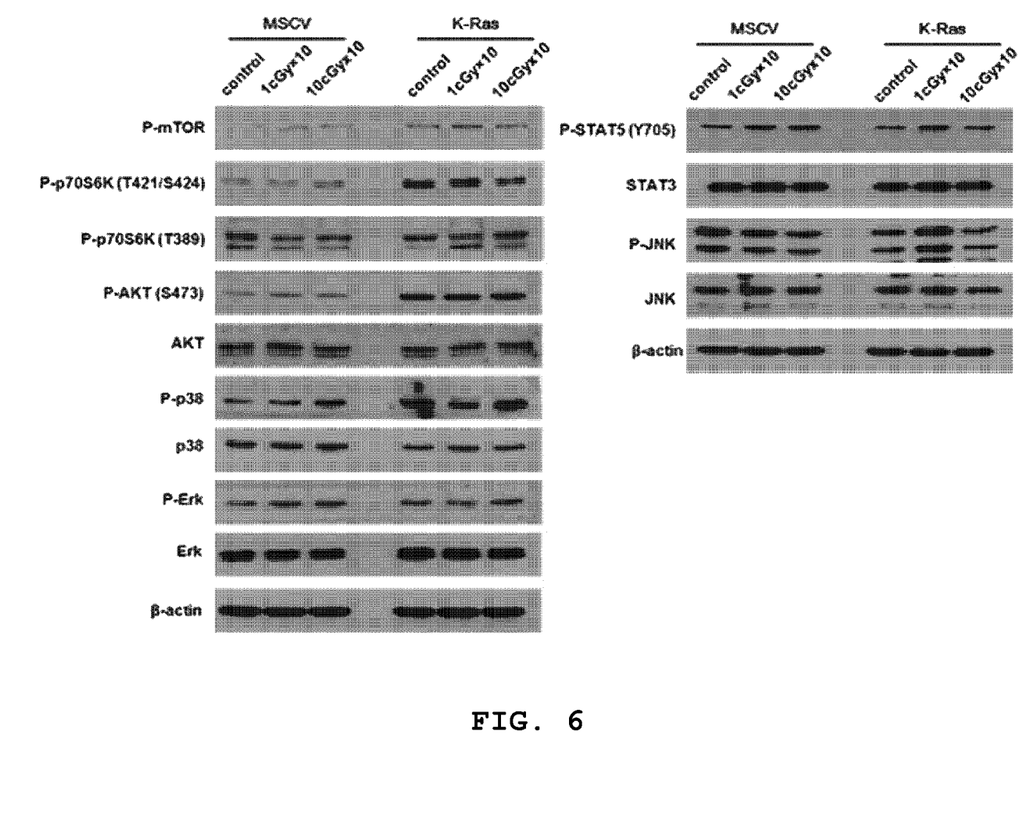
FIG. 6 shows the result of western blotting assay for the expression and activity of key proteins, which play an important role in a signal transduction system, in order to evaluate changes in the cells when using radiation.

In order to evaluate changes in the cells when using radiation, expression and activity of key proteins that play an important role in the signal transduction system were confirmed through western blotting assay. Although the activity of all signal proteins does not appear, low-dose radiation exhibits quite different changes from that of the control group or the high-dose radiation, indicating that malignant carcinogenesis can be concluded to be inhibited (FIG. 6).

Although the preferred embodiments of the present invention have been disclosed for illustrative purposes, those skilled in the art will appreciate that these embodiments are merely set forth to illustrate but are not to be construed to limit the scope of the present invention. Therefore, the substantial scope of the present invention will be defined by the appended claims and their equivalents.

What is claimed is:

1. An apparatus for inhibiting oncogene-induced malignant carcinogenesis, comprising an irradiation unit for applying low-dose radiation to a subject.

2. The apparatus of claim 1, wherein the low-dose radiation has a cumulative dose of 100 mGy or less but exceeding 0 mGy.

3. The apparatus of claim 1, wherein the oncogene is K-Ras.

4. The apparatus of claim 1, wherein the radiation is at least one selected from the group consisting of alpha rays, beta rays, gamma rays, electron rays, UV rays, and X-rays.

5. A method of inhibiting oncogene-induced malignant carcinogenesis, comprising the step of inhibiting an oncogene by applying low-dose radiation to a subject.

6. The method of claim 5, wherein the subject is a mammal other than a human.

7. The method of claim 5, wherein the low-dose radiation has a cumulative dose of 100 mGy or less but exceeding 0 mGy.

8. The method of claim 5, wherein the oncogene is K-Ras.

9. The method of claim 5, wherein the radiation is at least one selected from the group consisting of alpha rays, beta rays, gamma rays, electron rays, UV rays, and X-rays.

10. The method of claim 5, wherein the oncogene is inhibited by increasing expression of GP×4.

* * * * *